(12) United States Patent
Minter

(10) Patent No.: US 7,148,070 B2
(45) Date of Patent: Dec. 12, 2006

(54) DIAGNOSTIC DETECTION METHOD

(76) Inventor: Jimmy C. Minter, 716 Winters, Ft. Worth, TX (US) 76114

( * ) Notice: Subject to any disclaimer, the term of this patent is extended or adjusted under 35 U.S.C. 154(b) by 686 days.

(21) Appl. No.: 10/350,486

(22) Filed: Jan. 24, 2003

(65) Prior Publication Data

US 2004/0146428 A1    Jul. 29, 2004

(51) Int. Cl.
*G01N 33/48* (2006.01)
*G01N 33/493* (2006.01)
(52) U.S. Cl. .................. 436/169; 436/164; 436/901; 436/816; 436/810; 422/58; 422/61
(58) Field of Classification Search .............. None
See application file for complete search history.

(56) References Cited

U.S. PATENT DOCUMENTS

| | | | |
|---|---|---|---|
| 3,802,842 A | 4/1974 | Lange et al. ............... 23/253 |
| 4,960,467 A * | 10/1990 | Peck ..................... 252/408.1 |
| 5,111,539 A * | 5/1992 | Hiruta et al. .............. 4/661 |
| 5,244,631 A | 9/1993 | Morikawa ................. 422/56 |
| 6,087,185 A | 7/2000 | Lee-Own et al. .......... 436/514 |

* cited by examiner

*Primary Examiner*—Lyle A. Alexander
(74) *Attorney, Agent, or Firm*—Charles D. Gunter, Jr.

(57) ABSTRACT

The present invention relates to a diagnostic test kit and method for detecting the presence of certain metabolic by-products in human urine. The kit includes a test strip with an exposed face side containing chemical reagents which react in the presence of selected metabolic by-products. The reverse side of the test strip has an adhesive backing which allows the strip to be mounted in the interior of a commode bowl, initially above the water level. Flushing the commode causes the water level to rise and contact the chemical reagents. The reaction can be visually observed by removing the test strip from within the commode bowl.

6 Claims, 1 Drawing Sheet

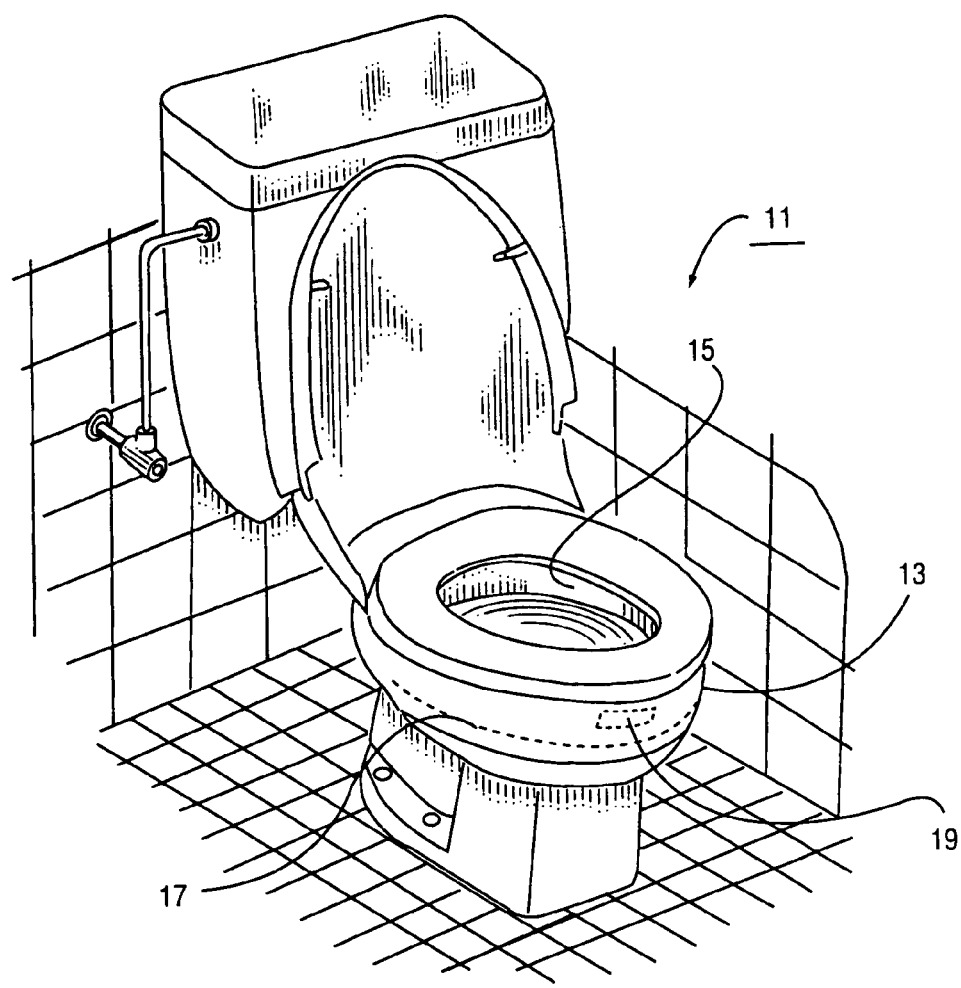
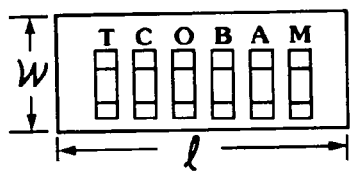
FIG. 1
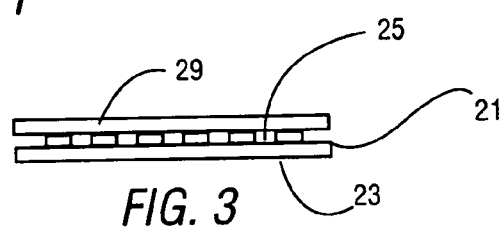
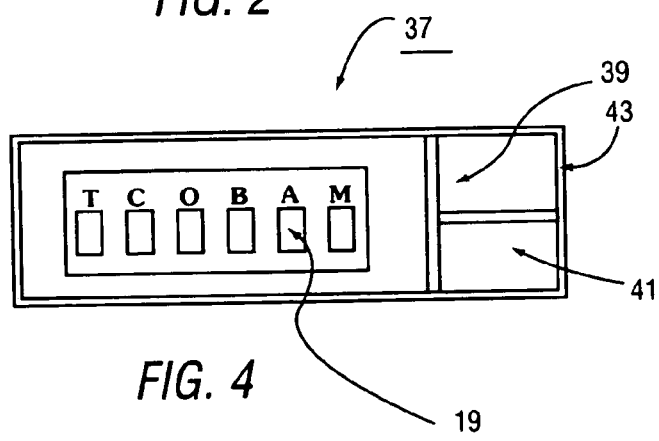
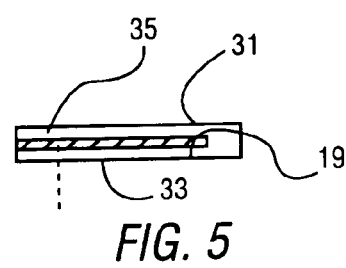

DIAGNOSTIC DETECTION METHOD

BACKGROUND ART

1. Field of the Invention

The present invention relates generally to assay/detection devices for detecting the presence of analyte in a field sample and, more specifically to an assay/detection device and method for detecting certain human metabolic by-products in toilet or urinal effluent.

2. Description of Related Art

Immunochromatographic assays, also called lateral flow tests or simply strip tests, are well known in the relevant arts. They are a logical extension of the technology used in latex agglutination tests, which have been available since the 1950's. The benefits of immunochromatographic tests include the fact that they are available in a user-friendly format, that only a short time is needed to obtain a result, that they exhibit long-term stability over a wide range of climates and that they are relatively inexpensive to manufacture.

These features make strip tests ideal for applications such as home testing, rapid point of care testing, and testing in the field for various environmental and agricultural analytes. In addition, they provide reliable testing that might not otherwise be available to third world countries.

The principle utilized in these tests is straightforward. Basically, any ligand that can be bound to a visually detectable solid support, such as dyed microspheres, can be tested for qualitatively, and in many cases even semi-quantitatively.

Immunochromatographic assays of the above type typically utilize a membrane as a solid support in a dipstick or flow-through device. These devices are available for drugs of abuse (cocaine, cannabinoid, amphetamines, opiates, PCP), pregnancy and fertility and infectious disease (chlamydia, Strep A, infectious mononucleosis, etc.). Some of the more common lateral flow tests currently on the market are tests for pregnancy, Strep throat, and Chlamydia. These are examples of conditions for which a quantitative assay is not necessary. The usual packaging for such assays is a membrane, typically cellulose, enclosed in a plastic holder. The device is then typically further packaged singly or in bulk in a sealed foil or plastic pouch which acts as an environmental control.

The plastic holder keeps the membrane in a suitable configuration in order to ensure correct functioning of the entire device. The usual test procedure involves opening the outer packaging and removal of the plastic device, followed by application of a sample through a sample window by dipping the device into the sample or by dropping the sample onto the sample window. After waiting the recommended amount of time, the results can be checked by checking the sample window for a positive or negative result. The result is typically indicated by a change in color of the test strip.

In the case of human metabolic by-products, the foregoing procedure assumes that a sample of urine is available for testing. In some cases, it may be advantageous to collect a sample or carry out a diagnostic test of urine without the knowledge of the subject being tested. Uses for this system would provide a screening or monitoring system for parents, counselors, coaches or other interested individuals.

There exists a need, therefore, for a diagnostic detection device and method which is inexpensive to manufacture, which provides at least a qualitative indication of the presence of a specific analyte and which can be administered in a relatively unobtrusive fashion.

There exists a need for such a diagnostic detection device which can be mounted quickly and easily within a commode or urinal, which device will provide an indication of the presence of a specific analyte upon flushing the commode or urinal.

There exists a need for such a device and method which can be used to test for the presence of the metabolic by-products of controlled substances including tetrahydrocannabinol, cocaine, opiates, barbiturates, amphetamine and methamphetamine.

SUMMARY OF THE INVENTION

The foregoing needs are met by the method and device of the present invention. The method of the invention can be used for detecting metabolic by-products of drug use in commode/urinal effluent. A test strip is mounted, for example, within a commode. The commode has a bowl with a bowl interior, the interior being partly filled to a water line with flush water. The test strip is mounted at a selected location within the bowl which is initially above the water line of the flush water, the test strip having applied thereto at least one diagnostic reagent which is activated by flush water containing urine. The test strip is removed after the commode has been flushed by a user and visually examined to determine if the diagnostic reagent has been activated by contact with the urine in the flush water to give a positive indication of the presence of the analyte in question.

Preferably, the test strip is comprised of a base strip having a planar adhesive face and an opposite planar exposed face, the exposed face having the chemical reagent applied thereto which is activated by flush water containing urine. The adhesive face allows the strip to be mounted within a commode or urinal in an unobtrusive fashion which would not normally be easily observed.

Preferably, a plurality of diagnostic reagents are applied to the exposed face of the test strip and the exposed face of the strip is at least partly encapsulated with a synthetic polymeric cover layer. A suitable cover layer can be formed of a polyolefin, such as polyethylene. In one embodiment of the invention, the stip is completely encapsulated except for and end opening of the cover layer. The encapsulation serves to prevent the diagnostic chemicals from being washed over and removed or overly diluted when the commode is flushed. A fabric strip can also be mounted on a selected face of the test strip, the fabric strip serving to wick flush water into contact with the diagnostic chemicals present on the exposed face of the test strip when the commode is flushed.

The test strip can also be packaged so that it is initially sealed within a pouch which also contains an initially encapsulated foaming agent which foams in the presence of urine. The foaming agent encapsulation is broken and the foaming agent is added to the flush water initially contained in the commode bowl prior to flushing. Suitable foaming agents can comprise, for example, sodium hypochlorite solution and calcium hypochlorite powder. Additional facilitating agents, such as a suitable surfactant, can also be included in the packaging.

Additional objects, features and advantages will be apparent in the written description which follows.

BRIEF DESCRIPTION OF THE DRAWINGS

FIG. 1 is a perspective view of a household commode having a test strip of the invention mounted therein, the test strip being indicated in dotted lines;

FIG. 2 is front planar view of a test strip of the invention showing the location of the chemical reagents thereon;

FIG. 3 is simplified, cross-sectional view of the test strip of FIG. 2;

FIG. 4 is a front view of a test strip of the invention enclosed in a packaging pouch; and FIG. 5 is a side, cross-sectional view of the packaged pouch of FIG. 4.

DETAILED DESCRIPTION OF THE INVENTION

The diagnostic test strip and method of the invention are used to screen and detect metabolic by-products present in human urine. The inventive method was developed as a part of a test program initiated to determine the feasibility of drug screening by testing the discharge of urine into a commode or urinal fluting during flushing. A special test strip was developed for this purpose. The results obtained from testing using the present system can be used to provide a screening or monitoring system for parents, counselors coaches or other interested individuals. The recovery of the discharged effluent used in the diagnostic method has only qualitative values because the actual urine sample dilution is uncontrolled to some extent and no attempt is made to determine the actual dilution rate of water to urine. For the design and purpose of this test strip, the exact dilution ratio is not critical, however. The system of the invention will identify the probable use of drugs or that a person is not using drugs. The confidence limit for this test device will provide an adequate probability that a person either is or is not using drugs. If the person tests positive, then a further laboratory test of the urine using thin layer chromatography (TLC) would be appropriate for example, for legal confirmation in court.

Applicant's testing proves the feasibility of sampling urinary discharges from commodes using a test strip device activated by the flushing of the commode. In conjunction with the test strip itself, a foam-enhancing agent is added to the toilet bowl at the time the test strip device is mounted inside the bowl above the water line. As will be explained with respect to the test data which follows, the system is workable and produces positive results with no false positives being observed. The testing which Applicant has performed, to date, has utilized NicAlert™ test strips to yield positive, negative or inconclusive results. In testing 215 urine samples, there have been 96.74% correct responses with 3.26% inconclusive. These test strips have been used since they test an additive, legal substance that does not require the use of DEA licensed laboratory to use controlled substances in testing. Test data includes controls of non-subjects as negatives and positives.

Test results from the commode flushing indicate that urine samples during flushing will respond on the test strips. Tests to determine the necessary sensitivity show that between three (3%) and five (5%) percent concentration of the normally discharged urine will activate a positive response. Cotinine from two subject's urine are in the greater than 1000 nanograms per milliliter (PPB, parts per billion) concentration. These subjects have demonstrated that cotinine in the 100 ngm plus range will produce a measurable response above the blank and negative subjects. This provides a base for use in establishing specific sensitivities for use in the case of illicit drugs such as opiates, amphetamines, alkaloids, cocaine, and PCP.

Tests show that sample mounting in the commode is critical to avoid a washout of the test strip reagents. The test strips have an adhesive backing to allow the strips to be easily mounted within the toilet bowl. Adherence to the test strips to the toilet bowl surface has not been a problem. A number of different adhesives have been tested. When device is affixed to a dry surface, it adheres until removed for the interpretation of test results. Washout is prevented with proper encapsulation of the test strips prior to insertion in the commode or urinal, however. In addition, the drug test device will use an exposed fabric when mounted to wick the solution of water and urine into the test strip chemicals to prevent washout when the commode is flushed.

In order to increase reliability of the test, adding a foaming agent to the test kit provides increased foaming in the urine; hence, improving concentration of the urine in the top layer of the urine and water solution and consequently providing a more uniform and delayed movement of the urine into solution within the water in the commode bowl. With the flushing of the commode, the commode's water movement moves the higher concentration of urine and water to the test strip, which has been secured above the stationary water level in the bowl. A small portion of sodium hypochlorite solution (ordinary household beach 4 ounces) or small amount of calcium hypochlorite (HTH, used in swimming pool maintenance) will be included with each test kit to be emptied into the toilet water. Either of these reacts with the urea to produce nitrogen gas and carbon dioxide as a very minute foam which concentrates the solids in the urine near the surface. This action improves the reliability of the test.

Testing of bleach, toilet bowl cleaning tablets, and other household cleaners has shown that these commonly used maintenance items do not affect the test results of the NicAlert™ test strip. Neither residue nor normal concentrated amounts per directions inhibit the desired function of Applicant's test strips.

FIG. 1 shows a common household commode or toilet 11. The toilet has a porcelain bowl 13 with an open interior 15. The interior 15 is partly filled with flush water to a stationary water line (shown as 17 in dotted lines in FIG. 1). A test strip 19 of the invention is shown mounted within the bowl interior 15 at a selected location which is initially above the water line 17 of the flush water. The test strip has applied thereto at least one chemical reagent which is activated by flush water containing urine.

As shown in greater detail in FIGS. 2 and 3, the preferred test strip 19 has a width "w" of approximately 2.5 cm and a length "l" of approximately 65 mm. As shown in FIG. 3, the strip 19 can comprise a base strip 21 having a planar adhesive face 23 and an opposite planar exposed face 25. The opposite exposed face 25 has applied thereto at least one diagnostic chemical 27 which is actuable by flush water containing human urine to give a diagnostic indication of the presence of certain metabolic by-products in the presence of urine. In the example shown in FIG. 3, the strip 21 has applied thereto a plurality of different diagnostic chemicals. These chemical reagents are labeled as "TCOBAM" in FIG. 2 and represent the following drug and drug related metabolic by-products:

| | | |
|---|---|---|
| THC(9-tetrahdrocannabinal) | T | 11-& 9-tetrahydrocannabinol |
| Cocaine | C | Benzoylecgonine |
| Opiates | O | Morphine-3-glucuronide & morphine |
| Barbiturates | B | Metabolic derivatives |
| Amphetamine | A | Unconverted amphetamine, |

| | | |
|---|---|---|
| Methamphetamine | M | hydroxylated and deaminated derivatives Amphetamine, hydroxylated and deaminated derivatives |

The base strip itself may be comprised of a membrane type material such as a suitable cellulose which will allow wicking of the flush water. Alternatively, the base strip may be a basically impermeable material and a fabric type wicking material 29 may be mounted over the exposed face 25 of the strip in order to bring the flush water into contact with the diagnostic chemicals present on the exposed face 25 when the commode is flushed.

As shown in FIGS. 4 and 5, the exposed face of the test strip 19 is preferably at least partly encapsulated with a synthetic polymeric cover layer. Most preferably, the entire strip is encapsulated by plastic laminate layers 31, 33. A perforated tear line 35 is provided to allow a user to expose the end of the test strip 19. The encapsulation prevents the diagnostic chemicals from being washed over with flush water from the commode or urinal being tested.

As shown in FIG. 4, the test strip 19 can be enclosed in "kit" fashion within a pouch 37 which also contains an initially encapsulated foaming agent which foams in the presence of urine. In the example shown in FIG. 4, the encapsulated region 39 contains approximately 10 grams of sodium lauryl sulfate, region 41 contains approximately 10 grams of calcium hypochlorite (HTH) and the pouch is an aluminum laminate plastic pouch with heat sealed seams 43.

TESTING CONCEPT

Testing of the concept has used NicAlert™ media. Use of NicAlert™ media serves these purposes: first, the test strips are readily available in quantity; second, there are many test subjects and locations readily accessible; third, there is no need to purchase regulated drugs when this test strip can be used to validate the inventive concept on a legally available and used drug; and fourth, the need for an FDA approved laboratory for drugs and testing is eliminated. The NicAlert™ device provides the needed data related to the quantitative requirements of the detection devices.

Using these strips, smokers are found to discharge greater than 1000 parts per billion (ppb) of cotinine. Cotinine is a metabolic waste of metabolized nicotine. The commode flush dilutes this to between 30 to 150 ppb of cotinine or a dilution of 3% to 15% of the discharged urine concentration. The specific sensitivities will depend upon the particular analyte being tested. For example, if amphetamines need to be under 25 ppb, the sensitivity of the test strips will need to be on the order of 0.05 to 0.07 ppb. Heroine on the other hand has about the same sensitivity as cotinine, i.e. greater than 1000 ppb.

As testing was initiated, it became readily apparent that a problem existed with the total wetting of the test device causing washout of the test strip agents. As a result, it was necessary to restrict the wastewater contact to a minimum to the strip. The ideal contact time needed is 3½ seconds to 10 seconds. Several configurations were tested with only partial success. Over 10% of the tests have were washouts, a washout being the flooding action of wastewater on these test strips. As a result of the washout problem, Applicant's test strips are sealed over the entire strip, except for the 5 to 10 millimeters required for activation of the strip. In one embodiment, a polyethylene pouch or envelope is used to encapsulate the test device to reduce or eliminate the washout problems.

Testing for the dilution threshold for reaction of the test device to give a position test is slightly more than 1% of discharged urine. At 1:1000 dilution, the tests are reported negative. The NicAlert™ test strips offer the capability of estimating the cotinine content in the sampled materials. As has been explained, the drug test embodiment of the test strip will be a positive or negative for drug use. This is a qualitative test as opposed to a quantitative test. In other words, the proposed drug test strips will be positive with drugs or metabolites present in the urine and negative for non-drug specimens.

Sample constraints for consistent test results for no washouts are established as follows: A test strip holder is necessary to initially encapsulate the test strips. Using polyethylene-wrapping material, the test strip is sealed with only the ends available to the flushed waters.

Test Procedures

Test strips are encapsulated in a watertight envelope opened only enough to permit the sample introduction area to be exposed to the water and urine during the flushing cycle. Foaming during the start of the flushing will be developed to aid in test chemical contact with the end of the test strip. The test procedure is comprised of four parts.

1. Test strip preparation: The first step comprises the removal of the test strips from the commercial packaging. These test strips are then bonded by contact adhesive to the test strip holders for mounting to the toilet surface for wastewater contact. A clean toilet bowl is used for testing.
2. Sampling procedure consists of attaching the adhesive backed test strip to the toilet in such a manner that it is not obvious to the casual user. The strip is attached in a manner that avoids allowing the water to be forced between the mounted test strip and the walls of the receptacle. Next these test strips are affixed to the porcelain surface of the toilet after the surface is wiped dry with a piece of toilet tissue. The test strip test section must not contact the water surface until flushing or urine contact occurs. The test strips are to be removed very shortly after exposure, i.e. flushing. It is imperative that the used water contacts these tests strips, not just flushing water from the toilet tank. The contact, for these NicAlert™ strips has been determined. Using an immersion of only 1 second is required to get valid results. The flushing normally takes 6 to 10 seconds to draw below the exposed sampling section of the test device. Additionally, the strip is mounted in a manner that the first water that contacts the test strip sampling section without forcing excessive water into these tests strips.
3. Urination occurs into the toilet bowl.
   Removal and reading of test strips. These test strips should be removed for evaluation against the NicAlert™ standard as soon as practical. Use of rubber gloves may be desirable. The indication of the test strip 3 will appear within the defined time as noted in the NicAlert™ instructions. The NicAlert™ test strips from previous tests have now been stored for eight weeks as of Sep. 25, 2002, with no change of color from the test result read early.

TEST RESULTS

Two hundred fifteen (215) tests runs to date have shown less than 36 false negatives with some of these being washouts. Some testing has involved urine testing using an accelerator as bleach or a detergent mentioned earlier to cause concentration of the urine in a foam complex near the top layer of the water delaying its equilibrium into solution. This gives a better exposure of this liquid mixture near the top of the surface to come into contact with the test strip first with its higher level of urine. Results of early tests showed 6.5% were blanks, 7.4% were non-smokers, and 86.1% were smokers. Only 3.256% of the test results were indeterminate. There were no false positive tests. A false positive test is where a known non-smoker tests positive with the NicAlert™ device.

Results of Test Device Mounting in Commode

| Index 2 | | | | Cotinine | | | | | | |
|---|---|---|---|---|---|---|---|---|---|---|
| Series # | | | | 2•Non- | | Results | | | False | 1•False |
| Index | Series | Total | Smoker | Smoker | Positive | Negative | Indefinite | Control | Positive | Negative |
| 2 | 1 | 18 | 8 | 10 | 5 | 13 | | 2 | 0 | 9 |
| 2 | 2 | 21 | 17 | 4 | 12 | 7 | 2 | 2 | 0 | 5 |
| 2 | 3 | 22 | 18 | 4 | 12 | 8 | 2 | 2 | 0 | 6 |
| 2 | 4 | 27 | 27 | 0 | 14 | 11 | 2 | 0 | 0 | 11 |
| 2 | 5 | 23 | 23 | 0 | 22 | 1 | 0 | 0 | 0 | 1 |
| 2 | 6 | 32 | 28 | 4 | 27 | 4 | 1 | 0 | 0 | 0 |
| 2 | 7 | 24 | 20 | 4 | 18 | 6 | 0 | 4 | 0 | 4 |
| 2 | 8 | 24 | 20 | 4 | 20 | 4 | 0 | 4 | 0 | 0 |
| 2 | 9 | 24 | 24 | 0 | 24 | 0 | 0 | 0 | 0 | 0 |
| Totals | | 215 | 185 | 30 | 154 | 54 | 7 | 14 | 0 | 36 |

Footnote 1••••A false negative is where a known user of tobacco tests negative due to in sufficient metabolism of the nicotine into cotinine at the time of urination.
Footnote 2••••Fourteen (14) of the non-smokers were controls or water only tests.

An invention has been provided with several advantages. The test strips of the invention provide a convenient, reliable and inexpensive diagnostic screening tool for making a qualitative finding of probable drug use. This provides a useful screening tool for concerned parents, counselors, coaches or other interested parties. The test strips can be easily installed in an unobtrusive location within a common commode or urinal. Test results are immediately available by simple visual observation without the necessity of sending a sample to a lab. The same test procedure could be used for a variety of other types of testing with little modification, such as testing for pregnancy or certain infectious diseases.

I claim:

1. A screening method for detecting metabolic by-products of drug use in commode effluent, the method comprising the steps of:
    mounting a test strip within a commode, the commode having a bowl with a bowl interior, the interior being partly filled to a water line with flush water, the test strip being mounted at a selected location within the bowl which is initially above the water line of the flush water, the test strip having applied thereto at least one diagnostic chemical which is activated by flush water containing urine;
    removing the test strip after the commode has been flushed by a user and visually examining the test strip to determine if the diagnostic chemical has been activated by contact with the urine in the flush water; and
    wherein the test strip has an adhesive backing and the strip is secured in position within the commode bowl by adhesively attaching the backing to the material of the commode bowl.

2. The method of claim 1, wherein the diagnostic chemicals are applied to an exposed face of the test strip and wherein the exposed face of the strip is encapsulated except for an end opening with a synthetic polymeric cover layer which prevents the diagnostic chemicals from being washed over when the commode is flushed.

3. The method of claim 2, wherein the synthetic polymeric cover layer is formed of a polyolefin.

4. The method of claim 1, wherein a fabric strip is mounted over the exposed face of the test strip, the fabric strip serving to wick flush water into contact with the diagnostic chemicals present on the exposed face of the test strip when the commode is flushed.

5. A screening method for detecting metabolic by-products of drug use in commode effluent, the method comprising the steps of:
    mounting a test strip within a commode, the commode having a bowl with a bowl interior, the interior being partly filled to a water line with flush water, the test strip being mounted at a selected location within the bowl which is initially above the water line of the flush water, the test strip having applied thereto at least one diagnostic chemical which is activated by flush water containing urine;
    removing the test strip after the commode has been flushed by a user and visually examining the test strip to determine if the diagnostic chemical has been activated by contact with the urine in the flush water; and
    wherein the diagnostic chemicals are activated by the presence of the by-products of controlled substances in the flush water, the controlled substances being selected from the group consisting of tetrahydrocannabinol, cocaine, opiates, barbiturates, amphetamine and methamphetamine.

6. A screening method for detecting metabolic by-products of drug use in commode effluent of a test subject, the method comprising the steps of:

mounting a test strip within a commode, the commode having a bowl with a bowl interior, the interior being partly filled to a water line with flush water, the test strip being mounted at a selected location within the bowl which is initially above the water line of the flush water, the test strip having applied thereto at least one diagnostic chemical which is activated by flush water containing urine of the test subject;

removing the test strip after the commode has been flushed and visually examining the test strip to determine if the diagnostic chemical has been activated by contact with the urine in the flush water;

wherein the test strip is initially contained within a pouch which also contains an initially encapsulated foaming agent which provides increased foaming of the urine, thereby improving the concentration of urine in the flush water and consequently providing a more uniform and delayed movement of urine into solution within the flush water in the commode bowl.

wherein the foaming agent encapsulation is broken and the foaming agent is added to the flush water initially contained in the commode bowl prior to flushing; and wherein the foaming agent is selected from the group consisting of sodium hypochlorite solution and calcium hypochlorite powder.

* * * * *